(12) United States Patent
Yates et al.

(10) Patent No.: US 6,467,424 B1
(45) Date of Patent: Oct. 22, 2002

(54) SUBMERSIBLE SYSTEM FOR ANALYZING UNDERWATER HABITAT QUALITY

(75) Inventors: Kimberly K. Yates, Apollo Beach, FL (US); Robert B. Halley, St. Petersburg, FL (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 0 days.

(21) Appl. No.: 09/874,232

(22) Filed: Jun. 6, 2001

(51) Int. Cl.[7] .......................... B63C 11/00; E04H 15/44
(52) U.S. Cl. ...................... 114/312; 114/314; 119/208; 119/211; 135/124; 135/125; 135/128; 135/137
(58) Field of Search ................................. 114/312, 314; 119/207, 208, 211; 135/124, 125, 128, 137

(56) References Cited

U.S. PATENT DOCUMENTS

| | | | | |
|---|---|---|---|---|
| 3,851,487 A | * | 12/1974 | Lambertsen | 114/257 |
| 4,000,749 A | * | 1/1977 | Busco | 135/117 |
| 4,047,390 A | * | 9/1977 | Boyce, II | 405/188 |
| 5,595,203 A | * | 1/1997 | Espinosa | 135/123 |
| 5,660,002 A | * | 8/1997 | Lashinger | 135/119 |
| 5,765,584 A | * | 6/1998 | Heisler et al. | 135/117 |

* cited by examiner

Primary Examiner—Sherman Basinger
(74) Attorney, Agent, or Firm—Ross F. Hunt, Jr.

(57) ABSTRACT

A submersible system is provided for isolating a volume of water located above an underwater substrate and for analyzing the volume of water. The system includes a tent having a shape enclosing an area of underwater substrate and a volume of water immediately above the substrate. A support frame formed by frame members each including plural detachable sections for maintaining the shape of the tent. A securing assembly, comprising a peripheral flap held down by weights in the form of sandbags or a heavy chain serves to secure the tent to the substrate. A circulation system, located at least partially within the tent, provides circulation of the volume of water within the tent so as to maintain a circulating flow pattern within the tent. A flow through analytical system is provided for removing a portion of water from the enclosed volume of water and for analyzing at least one property of the portion of water.

24 Claims, 2 Drawing Sheets

SUBMERSIBLE SYSTEM FOR ANALYZING UNDERWATER HABITAT QUALITY

BACKGROUND OF THE INVENTION

1. Field of the Invention

The present invention relates to submersible systems for monitoring and experimentation in aqueous ecosystems. More specifically, the present invention relates to a portable submersible in situ system for monitoring of, and experimentation with respect to coral reef ecosystems, coastal ecosystems and fisheries.

2. Related Art

The dangers to aqueous ecosystems from pollution and other processes are apparent, as is the need to act to preserve these ecosystems. Interest in gathering information on the processes and restoration of aqueous ecosystems, as well as interest in gathering information by experimentation on the effects of environmental perturbation on aquatic habitats, has greatly increased. This information is critical for assessing the health of aquatic ecosystems, for assessing environmental restoration progress, and for predicting the response of these ecosystems to climate change and declining water quality from natural and man-made influences.

In situ experiments measuring metabolic and geochemical processes associated with underwater organisms have been performed using very small (<0.5 m diameter, <4 liter volume) incubation chambers constructed of rigid Plexiglas or acrylic glass. These chambers effectively isolate a small volume of water about individual or small groups of underwater organisms enabling short-term (typically several minutes to a few hours) incubation experiments. These small chambers provide valuable information on processes associated with individual underwater species. However, accurate measurements of community level responses cannot be achieved using these small chambers. Additionally, these small chambers are not versatile and cannot be adjusted for size or volume to accommodate variations in substrate topography. These rigid chambers are limited in size due to difficulties in transporting and deploying larger chambers and in conforming and sealing the chambers to the often uneven substrate.

Community scale measurements of metabolic and geochemical processes have generally been performed using a technique called the "upstream/downstream" approach. This technique measures spatial geochemical changes in the water column along transects (generally greater than 100 m) across the substrate at the upstream and downstream ends of each transect. Currents/water circulation at the study site must be well characterized using current meters or other water mass tracking techniques. This method assumes conservation of water mass along transects, and is, therefore, limited to areas where unidirectional currents can be identified. Difficulties in accurately tracking the movement of a water mass result in the potential for a large margin of error. Many coastal ecosystems, such as coral reefs, have a complicated topography resulting in complex water circulation patterns. Thus, use of this technique is severely limited in its application.

Twenty-four hour monitoring along transects is logistically difficult due to problems in navigating along transects during dark hours. Most importantly, the upstream/downstream technique is limited by the resolution of geochemical measurements. Water must reside over the substrate long enough for its chemistry to be affected by processes of interest. Faster water flow rates result in shorter residence times and require a higher resolution for geochemical measurements to detect smaller chemical changes. Slower flow rates increase residence time of water over the substrates but most underwater organisms alter their metabolism when flow rate decreases, producing an abnormal response.

Structures resembling tunnels have been used to divert water flow in a modified upstream/downstream method. However, it has been found to be difficult to divert water flow over the long distances (100's of meters) typically required for accurate geochemical measurements with this method.

Therefore, there is a need in the art for a system that is portable, yet capable of accurately monitoring underwater habitats of various topography and currents therein at the individual organism, or community level.

SUMMARY OF THE INVENTION

According to the present invention, a portable system is provided for isolating, in situ, a large volume of water overlying a substrate in various aqueous environments. The system is designed to isolate the volume of water from the ambient aquatic environment, while maintaining contact between the captured volume of-water and the substrate components beneath it, including sediments and living organisms. The system provides for situ monitoring of physical and chemical characteristics of the water volume, monitoring of the components of the water, and associated monitoring of underwater organisms and substrates. Additionally, the system can be used for in situ manipulation of the physical and chemical parameters within the isolated volume of water for experimental investigations on the effects of environmental disturbances of the water, disturbances of components of the water, and disturbances of.the substrate.

In accordance with the invention, a submersible system is provided for isolating a volume of water located above an underwater substrate and for analyzing the volume of water, the system comprising: a tent having a shape enclosing an area of underwater substrate and a volume of water immediately above the substrate; support means for maintaining the shape of the tent; securing means for securing the tent to the substrate; a circulation system, located at least partially within the tent, for circulating the volume of water within the tent so as to maintain a circulating flow pattern within the tent; and a flow through analytical system for removing a portion of water from the enclosed volume of water, and for analyzing at least one property of the portion of water.

Preferably, analytical system includes means for returning the portion of water to the volume of water within the tent.

Advantageously, the submersible system further comprises means for removing trapped air from the tent.

Preferably, the tent further comprises a tent covering of a clear plastic material and at least one clear plastic tent door located at one end of the tent. Advantageously, the tent includes a further tent door located at the opposite end of the tent and the tent doors are attached by respective zippers to the tent covering. In a preferred implementation, the tent covering and the tent doors are comprised of a clear polyvinyl material. Preferably, the tent further comprises a bottom covering directly positionable on the substrate so as to separate the substrate from the volume of water.

The tent covering preferably includes a bottom peripheral flap extending outwardly therefrom so as to be positionable flat on the substrate and the securing means preferably comprises weight means positionable to provide weighing down of the flap so as to secure the flap in place. In one preferred implementation, the weight means comprises a plurality of sand bags, while in another, the weight means comprises a chain. In advantageous implementation, the flap comprises a reinforced flap extending outwardly from the bottom of the tent around the entire perimeter of the tent. In this implementation, the securing means advantageously comprises a plurality of sandbags located on top of the reinforced flap or a chain secured to the reinforced flap.

In a preferred embodiment, the support means comprises a tent frame comprising: a frame base for defining the substrate area enclosed by the tent; a plurality of frame ribs; a plurality of fittings on the frame base for attaching the frame ribs to the frame base; a frame spine; and a plurality of fittings on the frame spine for attaching the frame ribs to the frame spine. Advantageously, the frame base and frame spine each comprise a plurality of sections for enabling assembly and disassembly thereof. Preferably, the tent frame further comprises a plurality of metallic rods located within the frame base for assisting in maintaining the position of the frame upon the substrate. In this implementation, the frame base, the frame spine and the metallic rods each preferably comprise a plurality of sections for enabling assembly and disassembly thereof. Advantageously, the frame base, the frame ribs and the frame spine are comprised of polyvinyl chloride. Preferably, the frame base further comprises a plurality of pivoting stake supports. In a preferred implementation, the frame spine fittings comprise 90 degree fittings and the frame base fittings comprise T-fittings.

Other features and advantages of the invention will be set forth in, or will be apparent from, the detailed description of the preferred embodiments which follows.

DESCRIPTION OF THE PREFERRED EMBODIMENTS

Figure 1:
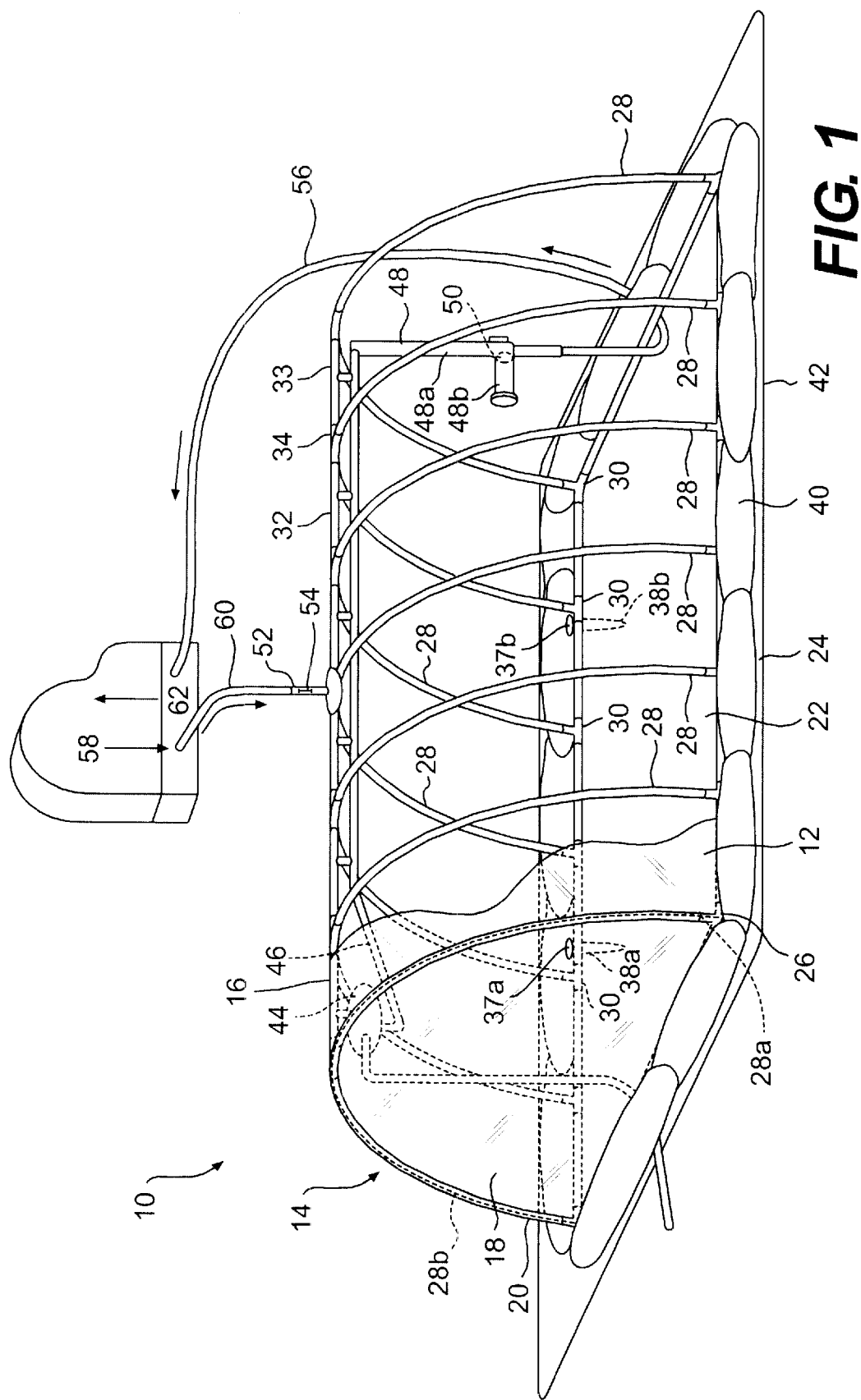
FIG. 1 is a perspective view of a submersible system constructed in accordance with a preferred embodiment of the invention, after assembly.
Figure 2:
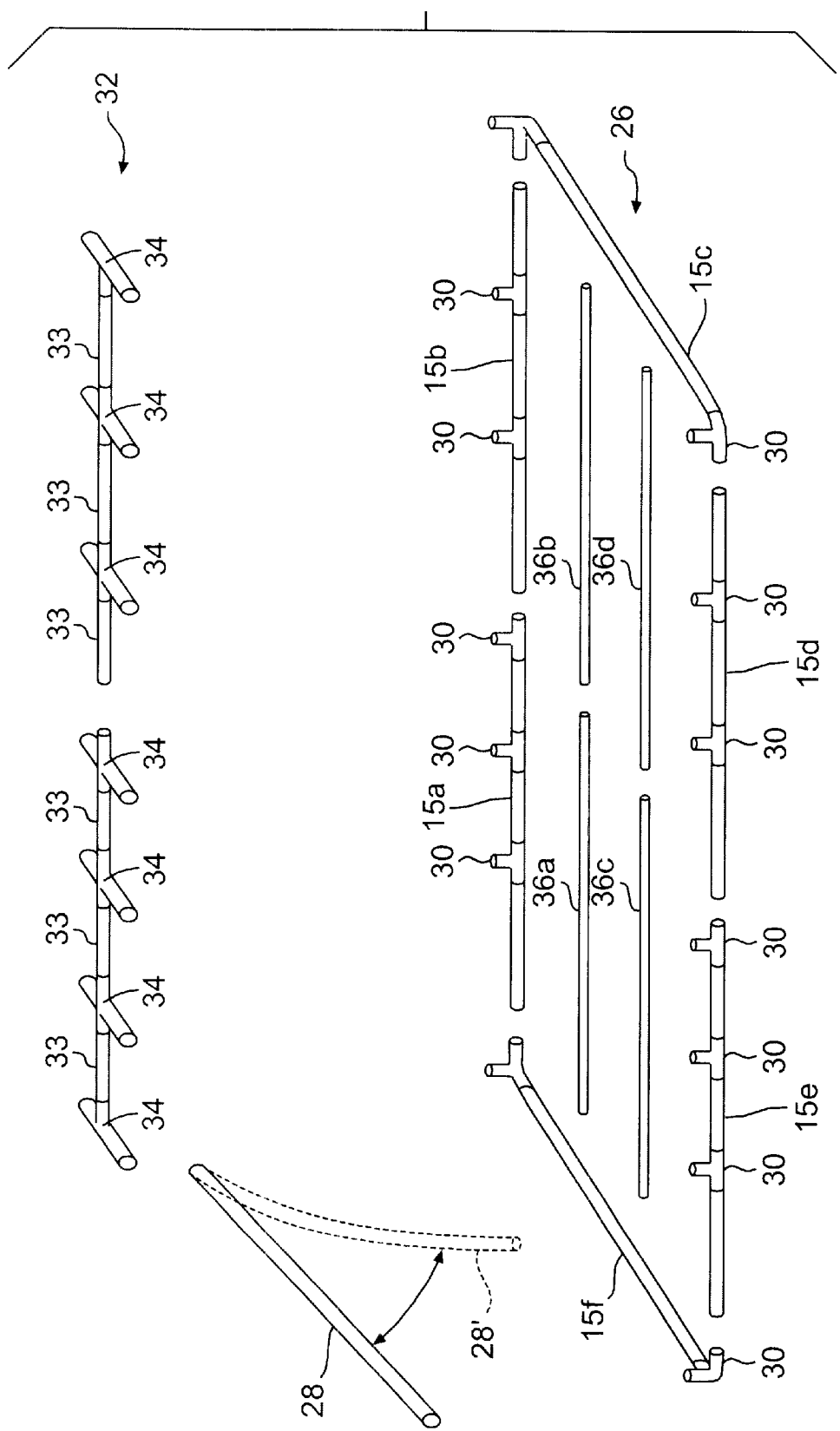
FIG. 2 is a perspective view of selected parts of the system of FIG. 1, before assembly.

Turning first to FIG. 1, the system of the invention includes a tent 10 for enclosing the volume of water. The tent 10 includes a tent covering 12 which is described below and which, in this embodiment, is supported by a polyvinyl chloride (pvc) tent frame 14. In a specific, non-limiting example, the dimensions of the tent frame 14 are 16 (l)×8 (w)×4 (h) feet, and the polyvinyl components are ¾ inch (diameter). As shown in FIG. 2, the tent frame 14 disassembles into eight foot sections for easy transport and reassembly.

Assembly of the frame 14 begins with assembly of a frame base 26. Six eight-foot sections, indicated at 15a, 15b, 15c, 15d, 15e and 15f and collectively denoted 15, are assembled to construct the frame base 26, which, in the exemplary embodiment under consideration, has dimensions of 16×8 ft. The frame base 26 can be constructed above water and subsequently lowered into place on the substrate, or assembled below water, e.g., by scuba divers. The frame base 26 has twelve pivoting stake supports, two of which, denoted 37a and 37b, are shown in FIG. 1 and which are collectively denoted 37. The stake supports 37 are adapted to hold three foot stainless steel stakes, two of which, denoted 38a and 38b, are shown in FIG. 1 and which are collectively denoted 38. The stakes 38 are driven into the substrate as an alternate method for maintaining position of the tent frame 14 on an irregular bottom.

As shown in FIG. 2, the tent frame 14 also includes two sets of two eight-foot sections of stainless steel rod 36a, 36b and 36c, 36d which are respectively connected together by male and female connecting ends. The connected rods are placed inside the pvc pipe sections 15 lengthwise to add weight to the frame 14, to maintain the position of the frame 14 on the bottom, and to prevent bowing of the frame base 26.

As shown in FIG. 1, the upper portion of tent frame 14 includes a frame spine 32 which, as shown in FIG. 2, comprises alternating straight pvc sections 33, and 90° pvc fittings 34, adapted to be joined together.

To complete the tent frame 14, fourteen frame ribs, two of which, denoted 28a and 28b, are shown in FIG. 1 and which are collectively denoted 28, are inserted into respective spaced T-fittings 30 of the frame base 26 (best seen in FIG. 2). As indicated for a single rib in FIG. 2, the ribs 28 are each bowed and inserted at the other end thereof into a respective 90° pvc fitting 34 on the frame spine 32. The frame ribs 28 thus each extend between a fitting 34 and a respective T-fitting 30 and, taken two at a time, an arch or bowed support structure.

After the frame 14 is assembled, the tent covering 12, which is preferably made of clear vinyl, is fitted over the assembled frame 14. A portion of the tent covering 12 is shown at the left side of FIG. 1. In non-limiting example, the tent covering 12 is 21 feet in length and 16 feet wide, and of sufficient size to cover the frame ribs 28. The center line of the tent covering 12 has a plurality of spaced grommet tabs 16, one of which is shown in FIG. 1, spaced every three feet along spine 32 for attaching the tent covering 12 to the spine 32. A pair of clear vinyl tent doors, one of which, denoted 18 is shown in FIG. 1, are attached to the tent covering 12 at opposite ends thereof in a final assembly step of the tent covering 12, using a pair of eighteen foot zippers, one of which, denoted 20, is shown in FIG. 1. The tent covering 12 and tent doors 18 enclose and isolate a volume of water therein. The approximate volume of the tent 10 after being assembled and having the dimensions described herein is 7,809 liters.

A clear vinyl floor 22 can be inserted between the substrate and the tent frame base 26 so as to provide a barrier between the enclosed volume of the water and the substrate. The addition of the floor 22 completely isolates the volume of water within the tent 10 from the substrate.

An arrangement is provided for securing the tent 10 to the substrate, so that the tent 10 remains firmly in place even when the substrate is uneven or of pitched slope. In this regard, in the preferred embodiment shown in FIG. 1, a peripheral reinforced seal flap 24 extends from the edge of the tent covering 12 and includes flap grommets (not shown) spaced apart approximately every foot in a row about the seal flap 24. A second row of grommets (not shown), is located near (e.g., about one inch from) the edge of the tent covering 12. These grommets can be used in conjunction with the first row of grommets to secure a chain (a small portion of which, denoted 42, is shown in FIG. 1) to the seal flap 24 and weigh the edges of the tent covering 12 down, while contouring the shape of the tent 10 to the bottom.

The tent 10 can also be secured in place on, and shaped or contoured to, the substrate by laying sandbags 40 around the perimeter thereof on the seal flap 24. The sandbags 40 may be provided in addition to, or as substitute for, the chain 42. In a specific non-limiting example, the sandbags 40 weigh 40–45 pounds and are constructed of five foot sections of drain sleeve filled with coarse grain sand, tied at one end, and cinched at the other end using zip ties (not shown). The sandbags 40 are laid on the seal flap 24 around the perimeter of the frame 14. The sandbags 40 are overlapped end-to-end so as to contour the shape of the flap 24 to substrate and, similarly to the chain 42, weigh the tent 10 down and hold the tent 10 in place along the bottom, thereby preventing leakage of water into or out of the tent 10.

A circulation system located within the tent 10 maintains water flow within the interior of the tent 10. As shown in the left hand portion of FIG. 1, this system includes a submersible 65 gpm (gallon per minute) circulation pump 44 which is mounted within the tent 10 on the frame spine 32. A 16 foot (L)×3 inch (diameter) circulation hose 46 is attached to the circulation pump 44 at one end thereof. As illustrated, the circulation hose 46 extends along the top central portion of the tent 10 and, in this regard, circulation hose 46 is attached to the frame spine 32 at (e.g., six) spaced points along its length. The pump hose 46 extends along the frame spine 32 from the circulation pump 44 to the opposite end of the tent 10, and the opposite end of the circulation hose 46, i.e., the end not attached to the circulation pump 44, is fitted to a 3 inch (diameter)×3 feet (L) pvc flow diversion tube 48. The flow diversion tube 48 is very roughly in the shape of the letter "C" and includes a downwardly depending portion 48a and an inwardly directed portion 48b which faces towards pump 44 and serves reversing the direction of flow. Specifically, the flow diversion tube 48 diverts water flow in a downward direction from the circulation hose 46 located at the top of the tent 10 and the flow is diverted once more by portion 48b of the flow diversion tube 48, so as to exit the flow diversion tube 48 while moving in a direction toward the circulation pump 44 located at the opposite end of the tent 10 and at a level lower than the water flowing from the circulation pump 44. This diversion of water flow creates a circular flow path or loop which maintains a current inside of the tent 10 and thus prevents the water therein from becoming stagnated. Advantageously, the flexible nature of the tent allows oscillatory water motion, generated naturally by waves, to be translated through the tent walls to the enclosed water mass inside. A combination of oscillatory water motion and circulating water inside of the tent provides the most natural water flow regime for enclosed organisms. It will be appreciated that stagnation of the water, if permitted, would alter the metabolic response of most aquatic and marine organisms.

A hose 56, which can comprise standard ¾ inch garden hose, is attached at one end of the flow diversion tube 48. The hose 56 is used as an outflow hose to carry a portion of the water from within the tent 10 to the surface for analysis. Flow to the hose 56 is controlled and directed by a ball valve 50 disposed within the flow diversion tube 48. The water is pumped by a second remotely located pump 62 from the outflow hose 56 to a remote analysis unit 58. An inflow hose 60 is also connected to pump 62 and is used to return water to the tent 10 after analysis. The analysis unit 58 is used for analyzing various properties of the water according to application and/or need. In this regard, the analysis unit 58 is capable of analyzing water properties such as pH, dissolved oxygen, and salinity, and of removing water samples from, and of injecting chemicals into, the volume of water as necessary. As is evident from the foregoing, water is pumped back into the tent 10 in a closed loop, with the second pump 62 returning the water back to the tent 10 through the inflow hose 60.

An air removal pipe 52 is attached to the top center of the tent 10 to expel air trapped during assembly of the system. In a specific non-limiting example, the air removal pipe 52 consists of a one foot section of ¾ inch pvc pipe with an associated ball valve 54, a hose fitting (not shown) attached to the top at the pipe 52, and first and second threaded plate fittings and associated first and second gaskets (not shown) at the bottom of the pipe 52. More specifically, while other sealed connections can be provided in accordance with this embodiment, the first plate fitting is threaded onto the pipe 52 from the outside of the tent 10 with the first gasket facing downwardly. The pipe 52 is inserted into a hole in the top center of the tent 10 with the pipe 52 facing outwardly. At this juncture, the second gasket and fitting plate are threaded from inside the tent 10. The gasket plates are tightened against the inside and outside of the tent 10, respectively, to prevent leaks. The inflow hose 60 is attached to the pipe 52.

The circulation system described above creates a horizontal flow across the tent 10 while the return flow from the inflow hose 60 of the water return system creates a slightly downward flow in the tent 10. The cross flows provide better mixing within the tent 10.

The tent 10 can be used to isolate large volumes of water over underwater communities to enable community-scale experimentation. Unlike the small incubation chambers referred to herein before, the tent 10 is versatile and can be adjusted in size to define different volumes and to accommodate a variety of substrate topographies.

The isolation of a mass of water provided by the system for monitoring and experimentation eliminates the need to track or follow a water mass over the substrate, as is required in upstream/downstream investigations of the prior art, and also eliminates the uncertainties of assuming conservation of water mass along transits. This results in more reliable analysis of community level processes. Further, water circulation can easily be altered in the volume defined by 10 for experimentation or standardized for experiment control. In addition, the system can be used to provide continuous, 24-hour monitoring of water mass and substrate ecosystem processes. Further, the system provides a mechanism for in situ alteration of environmental parameters such as salinity, turbidity, pH, and carbon dioxide content, thereby enabling investigations of the effects of environmental disturbances on underwater ecosystems.

In alternative embodiments of the invention to that described above include those providing variations in structural shape and size of the tent, and in the materials used in construction of the frame and tent, as well as modifications of frame style, the methods and mechanisms for weighting and sealing the tent to the substrate, and alternate methods and arrangements for providing water circulation within the tent structure.

It will be appreciated that the size of the tent 10, including length, width and height, of the tent, the volume of water used, and the flow rate of the circulation system, can easily be adjusted using the approach described above. The length and width of the frame 14 can be easily increased or decreased by replacing the existing sections with longer or shorter sections or omitting or adding sections. The height can be decreased or increased by using either shorter or longer ribs 28. The flow rate is readily increased or reduced by control of the ball valve 50 of the flow diversion tube 48. Further, the tent structure may be designed such that the tent 10 requires no frame. For example, the shape of the tent may be maintained using flotation devices or by connection of the tent body to fixed or floating permanent or non-permanent structures on the substrate or surface, e.g., stakes, pilings, moorings, buoys, hooks, and the like.

The invention can be advantageously used in, but is not exclusively limited to use in, the fields of aqueous geochemistry, biogeochemistry, biology and hydrology. The system of the invention can be used to investigate substrate/water interactions, sediment/water interface processes, ground water flux studies, entrapment and investigation of biological organisms, and the effects of biological organisms on water column chemistry.

EXAMPLES

Example 1

The system of the invention as generally depicted in FIGS. 1 and 2 was tested in both deep (greater than 40 feet) and shallow (less than four feet) water in the Gulf of Mexico. The field tests included fluorescein dye injection studies to examine leak rates and mixing rates in the system, deployment of current meters for measuring current characteristics generated by the circulation system, measurement of attenuation of photosynthetically active radiation by the clear vinyl covering 12 used to construct the tent 10, and 24-hour monitoring of the chemical changes in medium dense and heavily dense seagrass beds.

Fluorescein dye was injected into the tent 10 via a sample port in the flow through analysis unit 58 at night, and concentrations were monitored through the duration of the experiments using a model 10-AU Digital Fluorometer.

The data showed that approximately 24–30 minutes were required to mix water in the tent 10 and to reach peak dye concentrations. Results showed a slight decrease in fluorescein concentrations through dark hours consistent with rates of dye adsorption to sediments in organic materials, and concentration increases during light hours consistent with rates of photochemical decay of fluorescein. The rates of adsorption of dye to carbon sediment (2% of total concentration) and organic material (17% of total concentration) were used to generate a theoretical rate of concentration decay during the dark periods. This theoretical decay rate was used to correct raw fluorescence data to show decreases in night concentration associated with leakage of water into or out of the tent. Results showed no decrease in corrected dye concentrations. This indicates that there was no leakage of water during the incubation period. Fluorescein injection experiments indicated a water-mixing rate of approximately 24–30 minutes and no leakage at a circulation system flow rate of 65 gpm and a tent height of 4 feet.

Current speed and direction were measured in three dimensions. The results indicated that flow was not laminar and suggest that a turbulent flow may occur within the tent. The effects of the use of a clear vinyl sheeting or covering were examined by measuring attenuation of photosynthetically active radiation with water depth using a quantum sensor covered with a sleeve made from the same clear vinyl sheeting used to construct the tent covering for tent 10. The same measurements were performed with the sensor uncovered. Preliminary results indicate that no difference in attenuation occurs between sleeved and unsleeved sensor data below a depth of three feet.

Example 2

Twenty-four hour geochemical monitoring experiments were performed by deploying the system of the invention at a medium dense seagrass bed in a basin, and on a heavily dense seagrass in a separate basin. In these experiments, the height of the tent 10 was reduced from four feet to two feet to accommodate the shallow water in the basins. The isolated water volume was left in contact with the underwater substrate comprised of seagrass beds. Geochemical parameters of the isolated water volume, e.g., pH, dissolved oxygen, fluorescence, and temperature were continuously monitored using a flow-through analysis system throughout a 24-hour incubation period. Water samples were taken from the flow-through system every four hours and mixed with mercuric chloride for alkalinity measurements via Gran Titration. The rates of net calcification (carbonate sediment production), photosynthesis, and respiration (collectively referred to as production) were calculated for each four hour interval.

Sample rates at intervals were used to calculate daily average production rates. Dissolved oxygen and pH data trends were consistent with photosynthetic and respiratory activity of seagrass beds during light and dark intervals. Average daily rates of photosynthesis for the two basins were 0.6 and 1.25 g carbon $M^{-2}$ $day^{-1}$, respectively.

These are consistent with the range of values typically reported for seagrasses in the area of the basins. Calcification respiration calculations indicate net dissolution of 1.4 and 1.1 grams of calcium carbonate $m^{-2}$ $day^{-1}$. The net evolution of respired carbon was 0.2 grams $m^{-2}$ $day^{-1}$ in the first basin, and net uptake of carbon was 0.1 g $m^{-2}$ $day^{-1}$ in the second basin.

Although the invention has been described above in relation to preferred embodiments thereof, it will be understood by those skilled in the art that variations and modifications can be effected to these preferred embodiments without departing from the scope and spirit of the invention.

What is claimed is:

1. A submersible system for isolating a volume of water located above an underwater substrate located in a body of water and for analyzing the volume of water, said system comprising:
    a tent having a shape defining an enclosed tent volume for, in use, enclosing (i) an area of underwater substrate and (ii) a volume of water located immediately above the substrate and completely filling the enclosed tent volume when said submersible system is submerged in the body of water;
    support means for maintaining the shape of the tent;
    securing means for securing the tent to the substrate;
    a circulatory system located at least partially within the tent and disposed so as to provide circulation of the volume of water filling the enclosed tent volume throughout the enclosed tent volume so as to maintain a circulating flow pattern within the tent; and
    a flow through analytical system for removing a portion of water from the enclosed volume of water, and for analyzing at least one property of the portion of water.

2. A submersible system according to claim 1 wherein said analytical system includes means for returning the portion of water to the volume of water within the tent.

3. A submersible system according to claim 1, further comprising means for removing trapped air from the tent.

4. A submersible system according to claim 1, wherein the tent further comprises a tent covering of a clear plastic material and at least one clear plastic tent door located at one end of the tent.

5. A submersible system according to claim 4 wherein said tent includes a further tent door located at the opposite end of the tent and the tent doors are attached by respective zippers to the tent covering.

6. A submersible system according to claim 5, wherein the tent covering and the tent doors are comprised of a clear polyvinyl material.

7. A submersible system according to claim 4 wherein the tent covering includes a bottom peripheral flap extending outwardly therefrom so as to be positionable flat on the substrate and said securing means comprises weight means positionable to provide weighing down of said flap so as to secure said flap in place.

8. A submersible system according to claim 7 wherein said weight means comprises a plurality of sand bags.

9. A submersible system according to claim 7 wherein said weight means comprises a chain.

10. A submersible system according to claim 1, wherein the tent further comprises a bottom covering directly positionable on the substrate so as to separate the substrate from the volume of water.

11. A submersible system according to claim 1, wherein the tent further comprises a reinforced flap extending outwardly from the bottom of the tent around the perimeter of the tent.

12. A submersible system according to claim 11, wherein the securing means comprises a plurality of sandbags located on top of the reinforced flap.

13. A submersible system according to claim 11, wherein the securing means comprises a chain secured to the reinforced flap.

14. A submersible system according to claim 1, wherein said support means comprises a tent frame comprising:
   a frame base for defining the substrate area enclosed by the tent;
   a plurality of frame ribs;
   a plurality of fittings on the frame base for attaching the frame ribs to the frame base;
   a frame spine; and
   a plurality of fittings on the frame spine for attaching the frame ribs to the frame spine.

15. A submersible system according to claim 14 wherein said frame base and said frame spine each comprise a plurality of sections for enabling assembly and disassembly thereof.

16. A submersible system according to claim 14, wherein the tent frame further comprises a plurality of metallic rods located within the frame base for assisting in maintaining the position of the frame upon the substrate.

17. A submersible system according to claim 16, wherein the frame base, the frame spine and the metallic rods each comprise a plurality of sections for enabling assembly and disassembly thereof.

18. A submersible system according to claim 14, wherein the frame base, the frame ribs and the frame spine are comprised of polyvinyl chloride.

19. A submersible system according to claim 14, wherein the frame base further comprises a plurality of pivoting stake supports.

20. A submersible system according to claim 14, wherein the frame spine fittings comprise 90 degree fittings and wherein the frame base fittings comprise T-fittings.

21. A system as claimed in claim 1 wherein said circulatory system includes a pump and water inlet disposed at least close to an upper portion of the tent.

22. A submersible system for isolating a volume of water located above an underwater substrate located in a body of water and for analyzing the volume of water, said system comprising:
   a tent having a shape defining an enclosed tent volume for, in use, enclosing (i) an area of underwater substrate and (ii) a volume of water located immediately above the substrate and completely filling the enclosed tent volume when said submersible system is submerged in the body of water;
   support means for maintaining the shape of the tent;
   securing means for securing the tent to the substrate;
   a circulatory system located at least partially within the tent and disposed so as to provide circulation of the volume of water filling the enclosed tent volume throughout the enclosed tent volume so as to maintain a circulating flow pattern within the tent; and
   a flow through analytical system for removing a portion of water from the enclosed volume of water, and for analyzing at least one property of the portion of water,
   the tent further comprising a tent covering of a clear plastic material and at least one clear plastic tent door located at one end of the tent, and
   the tent covering including a bottom peripheral flap extending outwardly therefrom so as to be positionable flat on the substrate and said securing means comprising weight means positionable to provide weighing down of said flap so as to secure said flap in place.

23. A submersible system for isolating a volume of water located above an underwater substrate located in a body of water and for analyzing the volume of water, said system comprising:
   a tent having a shape defining an enclosed tent volume for, in use, enclosing (i) an area of underwater substrate and (ii) a volume of water located immediately above the substrate and completely filling the enclosed tent volume when said submersible system is submerged in the body of water;
   support means for maintaining the shape of the tent;
   securing means for securing the tent to the substrate;
   a circulatory system located at least partially within the tent and disposed so as to provide circulation of the volume of water filling the enclosed tent volume throughout the enclosed tent volume so as to maintain a circulating flow pattern within the tent; and
   a flow through analytical system for removing a portion of water from the enclosed volume of water, and for analyzing at least one property of the portion of water, and
   the tent further comprising a reinforced flap extending outwardly from the bottom of the tent around the perimeter of the tent.

24. A submersible system for isolating a volume of water located above an underwater substrate located in a body of water and for analyzing the volume of water, said system comprising:
   a tent having a shape defining an enclosed tent volume for, in use, enclosing (i) an area of underwater substrate and (ii) a volume of water located immediately above the substrate and completely filling the enclosed tent volume when said submersible system is submerged in the body of water;
   support means for maintaining the shape of the tent;
   securing means for securing the tent to the substrate;
   a circulatory system located at least partially within the tent and disposed so as to provide circulation of the volume of water filling the enclosed tent volume throughout the enclosed tent volume so as to maintain a circulating flow pattern within the tent; and
   a flow through analytical system for removing a portion of water from the enclosed volume of water, and for analyzing at least one property of the portion of water,
   said support means comprising a tent frame comprising:
   a frame base for defining the substrate area enclosed by the tent;

a plurality of frame ribs;
a plurality of fittings on the frame base for attaching the frame ribs to the frame base;
a frame spine; and
a plurality of fittings on the frame spine for attaching the frame ribs to the frame spine, and the tent frame further comprising a plurality of metallic rods located within the frame base for assisting in maintaining the position of the frame upon the substrate.

* * * * *